US009492585B2

United States Patent
Gibson et al.

(10) Patent No.: US 9,492,585 B2
(45) Date of Patent: Nov. 15, 2016

(54) CALCIUM PHOSPHATE MATERIAL

(71) Applicant: Sirakoss Limited, Edinburgh (GB)

(72) Inventors: Iain Ronald Gibson, Aberdeen (GB);
Janet Mabel Scott Skakle, Abderdeen (GB);
(Continued)

(73) Assignee: SIRAKOSS LIMITED (GB)

( * ) Notice: Subject to any disclaimer, the term of this patent is extended or adjusted under 35 U.S.C. 154(b) by 0 days.

(21) Appl. No.: 14/367,145

(22) PCT Filed: Dec. 17, 2012

(86) PCT No.: PCT/GB2012/053160
§ 371 (c)(1),
(2) Date: Jun. 19, 2014

(87) PCT Pub. No.: WO2013/093439
PCT Pub. Date: Jun. 27, 2013

(65) Prior Publication Data
US 2015/0024023 A1 Jan. 22, 2015

(30) Foreign Application Priority Data
Dec. 23, 2011 (GB) .................................. 1122405.2

(51) Int. Cl.
*C01B 25/32* (2006.01)
*A61L 27/12* (2006.01)
*A61L 27/56* (2006.01)

(52) U.S. Cl.
CPC ................ *A61L 27/12* (2013.01); *A61L 27/56* (2013.01); *C01B 25/32* (2013.01); *C01B 25/322* (2013.01); *C01B 25/327* (2013.01); *A61L 2400/12* (2013.01)

(58) Field of Classification Search
None
See application file for complete search history.

(56) References Cited

U.S. PATENT DOCUMENTS

| 6,013,591 A | 1/2000 | Ying et al. |
| RE44,820 E * | 4/2014 | Ying ....................... A61L 27/12 106/35 |
| 2010/0173009 A1 | 7/2010 | Gibson et al. |

FOREIGN PATENT DOCUMENTS

| DE | 10 2009 039665 A1 | 3/2011 |
| EP | 0 376 331 A2 | 7/1990 |

OTHER PUBLICATIONS

Sponer et al. In vivo behaviour of low-temperature calcium-deficient hydroxyapatite: comparison with deproteinised bovine bone, International Orthopedics (2011 ) 35:1553-1560.*
(Continued)

*Primary Examiner* — Robert A Wax
*Assistant Examiner* — Melissa Mercier
(74) *Attorney, Agent, or Firm* — Andrus Intellectual Property Law, LLP

(57) ABSTRACT

The invention relates to porous granular calcium phosphate osteoinductive materials, particularly materials useful in body tissue repair, principally bone repair and bone replacement, and also to the use of such materials and to a method of making such materials. Exemplary materials comprise discrete porous granules each containing crystals of at least one calcium phosphate, wherein (i) at least 90% of said crystals of the granules have a crystal size in the range 10-100 nm, (ii) at least 90% of the pores in the granules have a pore size in the range 10-500 nm, (iii) the average pore size of the pores having pore size in the range 10-500 nm in the granules is in the range 30-90 nm, (iv) the total volume porosity of the granules is at least 50%, and (v) the surface area of the granules is in the range 10-70 $m^2/g$.

13 Claims, 3 Drawing Sheets

(72) Inventors: Jordan Christopher Conway, Edinburgh (GB)

(56) References Cited

OTHER PUBLICATIONS

Sponer, P.A.A., et al., "In vivo behaviour of low-temperature calcium deficient hydroxyapatite: Comparison with deproteinised bovine bone," (2010) International Orthopaedics 35(10):1553-1560.
International Search Report and Written Opinion for International Patent Application No. PCT/GB2012/053160 dated Mar. 14, 2013 (13 pages).

* cited by examiner

CALCIUM PHOSPHATE MATERIAL

CROSS-REFERENCE TO RELATED APPLICATIONS

This patent application is a national stage filing under 35 U.S.C. 371 of International Application No. PCT/GB2012/053160, filed Dec. 17, 2012, which claims the benefit of priority of Foreign Patent Application No. GB1122405,2, filed Dec. 23, 2011, both of which are incorporated herein by reference in their entireties.

FIELD OF THE INVENTION

This invention relates to porous granular calcium phosphate materials, particularly materials useful in body tissue repair, principally bone repair and bone replacement, and also to the use of such materials and to a method of making such materials.

BACKGROUND OF THE INVENTION

Due to disease or trauma, surgeons need to replace bone tissue. They can use bone grafts (autografts or allografts) or synthetic materials to replace bone during surgery. Amongst the types of synthetic materials used to replace bone, surgeons use metals (e.g. stainless steel hip or knee implants), polymers (e.g. polyethylene in acetabular cups), ceramics (e.g. hydroxyapatite as a macroporous bone graft) or inorganic-organic composites (e.g. hydroxyapatite-poly(lactic acid) composites for fixation plates).

Calcium phosphate ceramics, such as hydroxyapatite or tricalcium phosphate, which are utilised as bone graft materials are typically produced by forming a macroporous structure, similar to that of cancellous bone. Such bone grafts typically have large values of total porosity (60-90%) with the porosity existing as a mixture of macropores (0.1 to 1 mm in size) and micropores (0.5 to 10 µm), with the macropores interconnected. These usually require high sintering temperatures, typically between 1100-1300° C., as part of the manufacturing process, to densify the calcium phosphates making up the porous 'cancellous' structure. Such a macroporous bone graft, typically used in granular form, is classed as osteoconductive, meaning that it acts as a scaffold and allows bone to grow along its surface. Unlike autografts, most synthetic calcium phosphate bone grafts are not osteoinductive. Osteoinductivity is the ability to induce new bone formation by directing undifferentiated mesenchymal stem cells to differentiate and form bone. Recently, some groups have reported developments of synthetic bone grafts based on calcium phosphates that are osteoinductive. The accepted test for osteoinductivity is the implanting of the bone graft material in a non-osseous (non-bone) site, either subcutaneously or intramuscularly in a suitable animal model, and using histology and histomorphometry determine if bone is formed in this site. A bone graft material that is only osteoconductive does not form bone in this site, whereas an osteoinductive material does form bone. The advantage of an osteoinductive bone graft is that, when implanted into a bone defect in humans, it will have an accelerated rate of bone repair because bone can form at the interface of the implant and host bone by an osteoconductive response, and also throughout the implant by an osteoinductive response. For new bone to form throughout an osteoconductive bone graft requires a longer time after implantation, as new bone migrates throughout the bone graft from the interface of the implant and host bone.

Osteoinductive calcium phosphate ceramics are disclosed in U.S. Pat. No. 6,511,510, describing calcium phosphate ceramics with a mixture of macropores with sizes between 0.1 to 1.5 mm and micropores with sizes between 0.05 to 20 µm, with a total porosity of between 20 and 90%, and a crystal size between 50 nm and 20 µm. These osteoinductive ceramics were formed using elevated temperatures of 1000-1275° C., preferably 1150-1250° C. The ceramic material is implanted as a block.

An osteoinductive calcium phosphate consisting essentially of microparticles with only micropores was described in US 2010/0034865 (U.S. Pat. No. 7,942,934), having micropores with sizes between 0.1 to 1.5 µm, with a surface area percentage of micropores of between 10 and 40% over the total surface of the granules, and a grain (crystal) size between 0.1 and 1.5 µm. These osteoinductive ceramics were formed using elevated temperatures of 1050-1150° C. In this patent, an example of granules that showed an osteoinductive response when implanted into the muscles of dogs that had the smallest micropores and grain (crystal) size was a tricalcium phosphate sintered at 1050° C.; values were reported as 0.58 µm pore size and 0.76 µm grain size, with a surface area percentage of micropores of 24.2%.

An inorganic resorbable bone substitute material with crystallites that are loosely held together rather than sintered together is described in DE 10060036. This material has a porosity consisting of three different size scales, with pores in the nanometer range, in the range of a few microns, and in the region of 100 to 1000 µm. The further disclosure US2007/0059379 (republished as US 2008/0152723) mentions the material described in DE 10060036, and combines calcium phosphate with a silica xerogel to form an inorganic resorbable bone substitute material that was stronger than the xerogel-free material. The silica xerogel has granule size of 1 to 1000 µm and the calcium phosphate has crystal size between 10 and 2000 nm. The xerogel has pores in the region of 0.5 to 20 nm, representing porosity of between 10 and 60%.

WO 2010/079316 describes an inorganic silicate-substituted calcium phosphate hydroxyapatite, which has the function of releasing high levels of silicon on soaking in solution, in order to stimulate formation of new bone. The CaP molar ratio is in the range 2.05 to 2.55 and the Ca/(P+Si) molar ratio is less than 1.66. The material is unsintered, and is used as a powder or a compacted powder. It is made by filtering a suspension of the compound, drying of the wet filter cake, grinding the dried cake to a fine powder and heating the powder at 900° C. Osteoinductivity was not tested.

US 2005/0191226-A1 (Tuan et al)—relates to a method for preparing hydroxylapatite powder. The hydroxylapatite powder was obtained by heating fish scales to temperatures including 600° C., 700° C., or 900° C. to remove the organic component and collecting the inorganic powder. The disclosure further relates to a hydroxylapatite porous body, which was obtained by sintering the hydroxylapatite powder. Osteoinductivity was not tested.

Grossin et al—(2010) "Biomimetic apatite sintered at very low temperature by spark plasma sintering: Physicochemistry and microstructure aspects". Acta Biomaterialia, vol. 6 (no 2). pp. 577-585 relates to spark plasma sintering, which was used to consolidate nanocrystalline apatites at non-conventional, very low temperatures (T<300° C.) so as to preserve the surface hydrated layer present on the nanocrystals. Bioceramic monoliths rather than granules were obtained.

U.S. Pat. No. 6,689,375 B1 (Wahlig et al)—relates to a resorbable bone implant material and method for producing the same. The powdery component of the implant material consists essentially of a mixture of hydroxyl apatite powder and calcium sulfate powder, wherein the hydroxyl apatite powder consists of synthetically prepared, precipitated crystalline nanoparticles, reported as having a crystal size of 10-20 nm width and 50-60 nm length. The specific absorbing BET surface area of the nanocrystals is reportedly, preferably, 100-150 $m^2/g$.

U.S. Pat. No. 6,013,591 (Ying et al) relates to methods for synthesis of nanocrystalline apatites. The disclosure reports a series of specific reaction parameters that can purportedly be adjusted to tailor the properties of the recovered product. Particulate apatite compositions having average crystal size of less than 150 nm are reportedly provided. It is stated that products can have a surface area of at least 40 $m^2/g$. Stated utilities for compositions are as prosthetic implants and coatings for prosthetic implants.

DISCLOSURE OF THE INVENTION

The aim of the present invention is to provide a calcium phosphate material which exhibits osteoinductivity and is easily produced.

The invention is based on the finding of a granular material having a defined nanoscale architecture which stimulates new tissue formation, principally bone repair. The material is osteoconductive, osteostimulatory and osteoinductive. Specifically, it is osteoinductive in that when implanted into a non-osseous (i.e. not a bone) site, such as intramuscularly or subcutaneously, it induces new tissue to form, principally new bone formation. It is believed that the osteoinductive properties of the compositions of the invention will translate to more rapid new bone formation/repair when implanted into an osseous site, so that new bone will form throughout the bone graft mass rather than at the edges of the bone graft mass where it is in contact with existing bone (as with known osteoconductive bone grafts).

The process of osteoinduction with the material described here may be associated with high levels of BMP-2 expression by cells prior to and during new bone formation. In particular, with the material described here, high levels of BMP-2 expression by vascular pericytes may be observed prior to formation of bone. During bone formation, with the material described here, high levels of BMP-2 expression by osteoblasts, osteocytes and fibroblasts around the granules may be observed. Relatively low expression of BMP-7 may be observed by cells around the granules prior to and/or during new bone formation.

In one aspect the invention provides a porous granular calcium phosphate material, comprising discrete porous granules each containing crystals (crystallites, crystal grains) of at least one calcium phosphate, wherein
  (i) at least 90% of said crystals of the granules have a crystal size in the range 10-100 nm, where the crystal size is the longest dimension of the crystal as seen in a cross-sectional SEM,
  (ii) at least 90% of the pores in the granules have a pore size in the range 10-500 nm, wherein the pore size is the largest dimension of the pore as seen in a cross-sectional SEM,
  (iii) the average pore size of the pores having pore sizes in the range 10-500 nm in the granules is in the range 30-90 nm, as measured by mercury intrusion porosimetry,
  (iv) the total volume porosity of the granules, measured using Archimedes's principle, is at least 50%, and
  (v) the surface area of the granules, measured by the BET method, is in the range 10-70 $m^2/g$.

Preferably at least 90% of the crystals have at least one dimension of not more than 50 nm as seen in a cross-sectional SEM. Preferably at least 90% of said crystals has at least one dimension in the range 20-40 nm as seen in a cross-sectional SEM.

Preferably the average ratio of the longest dimension of each crystal to the shortest dimension thereof is in the range 1-10, preferably in the range 1.5-3.

Preferably at least 50% of the pores in the granules have said pore size in the range 10-100 nm. Preferably said average pore size of the pores having pore sizes in the range 10-500 nm in the granules is in the range 30-70 nm.

Preferably the total volume porosity of the granules, is at least 60%, 65%, 70%, 75%, or 80%, more preferably in the range 70-90%.

Preferably the surface area of the granules is in the range 10-60 $m^2/g$, or 20-40 $m^2/g$.

Preferably said crystals of said granules are in a substantially unsintered state.

In another aspect, the invention consists in use of the calcium phosphate material of the invention described above as a bone graft material, a bone replacement material or a bone substitute material.

Further the invention consists in the calcium phosphate material of the invention as described above, for use in bone repair, by osteoinduction.

The invention also consists in a method of treatment of a mammal by bone growth, comprising placing a calcium phosphate material of the invention as described above at a site at which the bone growth is to take place.

The invention also provides a method of making a calcium phosphate material as described above, comprising the steps of:
  (a) preparing a dispersion of calcium phosphate crystals in a liquid phase,
  (b) partially removing the liquid phase to obtain a wet compacted mass comprising the calcium phosphate crystals,
  (c) drying said wet compacted mass obtained in step (b) so as to remove the liquid phase and obtain dried material in the form of a dry compacted mass comprising the calcium phosphate crystals, wherein the dry compacted mass has a total porosity of not less than 50%, as measured by Archimedes's method, prior to the heat treating step (d),
  (d) heat treating said dried material obtained in step (c), at a temperature in the range 200 to 1000° C., preferably 700 to 900° C., while substantially avoiding sintering of the crystals, and
  (e) before or after step (d), dividing the dry compacted mass into granules.

Preferably, in step (c) said total porosity of said dry compacted mass is not less than 60%, more preferably not less than 70%.

The material of the invention thus comprises calcium phosphate granules that have a specific architecture of each granule. Specifically, the size of the crystals that make up the granules (CS), the size of the pores throughout the granules (PS), the total porosity of the granules (TP) and the surface area of the granules (SA) are controlled by control of the processing parameters during production of the granules and these four parameters (CS, PS, TP and SA) have defined value ranges. The granule size may also be suitably controlled. This means that for a given calcium phosphate material, the processing parameters during production of the granules can be optimised to produce granules that have the appropriate values.

The material of the invention will be synthetic, by which is meant synthesised artificially by human intervention, or put another way, not derived from biological source materials e.g. fish scales. This permits more precise control of the parameters of the crystals, pores and granules as defined herein.

For the material of the invention, the parameters that are significant for the properties desired, are the size of the crystals that make up the granules (CS), the size of the pores throughout the granules (PS), the total porosity of the granules (TP) and the surface area of the granules (SA). The size of the granules (GS) may be determined by for example established methods of selecting size ranges of granules by sieving the material through a series of sieves of defined sizes.

In the invention, morphology of the crystals is preferably somewhat acicular in shape, so that one dimension of the crystal is longer than the other dimensions. The size (longest dimension) of the crystals that make up the granules (CS) is in the size range of 10 to 100 nm, or optionally 10 to 80, or 10 to 90 nm, with preferably at least one dimension of the crystals of a size less than 50 nm. Preferably, at least one dimension of the crystals has a size in the range of 20 to 40 nm. The ratio of the longest dimension to the shortest dimension (which is the shortest dimension in the direction perpendicular to the longest dimension) should be in the range of 1 to 10, preferably in the range of 1.5 to 3. The crystal size and morphology can be determined using scanning electron microscopy, in particular in an SEM of a cross-section (where the crystals are seen in two dimensions). As noted above preferably at least 90%, or at least 95%, of said crystals have this size range.

In the invention, the typical size (longest dimension) of the pores throughout the granules (PS) is in the size range of 10 to 500 nm. At least 90% of pores by number is in this size range. Preferably the majority (at least 50% by number) is in the size range of 10 to 100 nm.

The mean pore size is in the range 30 to 90 nm, preferably in the range 30-70 nm. The majority of pores are preferably within this size range of 30 to 90 nm, typically 60 to 100% of the pores lying within this size range, preferably more than 80% and most preferably more than 90%. While the material of the invention may have more than 95% of pores in this range, in practice there may be a number of larger pores. The mean pore size and pore size distribution is measured using mercury intrusion porosimetry.

Within the granules, there may be some large pores or voids of size greater than 500 nm, e.g. 1 µm or more. Such large pores or voids are excluded from the calculation of average pore size.

In the invention, the total porosity of the granules (TP) is such that in terms of volume, a greater volume of the granule is porosity than material. The total porosity of the granules is typically greater than 60%, and is preferably in the range of 70 to 90% of the total porosity. For clarification an example of the above could be that for a given granule, 70% of the granule is porosity, with the pores having a mean pore size of 30 to 70 nm, with the material component of the granule (for this example, the remaining 30% of the volume) composed of crystals with dimension in the range 10 to 100 nm, or optionally 10 to 80 or 10 to 90 nm, with at least one dimension of the crystals having a size in the range of 20 to 40 nm. This total porosity (TP) is measured using Archimedes's principle, as described in the ASTM C373.

In the invention, the surface area of the granules (SA) is higher than typical known calcium phosphate bone graft materials, due to the CS, PS and TP values as described above resulting in a material with a high specific surface area (expressed in $m^2/g$). The calcium phosphate material of the invention, with CS, PS and TP values as described above, has a specific surface area of between 10 and 70 $m^2/g$, preferably between 10 and 60 $m^2/g$, more preferably 20-40 $m^2/g$. The specific surface area (SA) is measured using the BET method, which utilises the adsorption of $N_2$ to the surface of the material.

In the invention, the size of the granules (GS) of the material, with the other four parameters (CS, PS, TP and SA) as described above, is typically in the range of 50 µm to 10 mm. Within this range, narrower particle size ranges may be selected, according to intended use, for example narrower ranges of 100-500 µm, 500-1000 µm, 1-2 mm, 2-5 mm, 5-10 mm, depending on the clinical application of the material as a bone graft system. While granule size range is typically within these ranges, the material of the invention may also have a narrower range, e.g. 200 to 300 µm, or may have granules of a range of size scales to affect the way that they are packed together. For example, a bimodal distribution may be appropriate for certain applications, such as granules having sizes in the ranges of 200 to 300 µm and 1 to 2 mm; the relative proportions of these may be designed to optimise their packing.

The upper and lower limits contained herein for the physical parameters of the granules, specifically crystal size for the calcium phosphate in the granules, the porosity features of the granules and the surface area of the granules, are chosen in order that the granular material shall have the effect of absorbing proteins which induce bone to form. The result is that new bone forms throughout the porosity of the granules. The crystal size is of importance for obtaining the nanoscale porosity features. The large surface area of the granules increase availability of sites for bone growth throughout the volume of the granules. The granule size can be selected according to intended use, as described herein. The granules having the selected size or sizes are discrete, being unjoined to each other, for delivery in this granular (particulate) form to the site where bone growth is wanted.

The term "calcium phosphate" is used in this specification, including the claims, to encompass numerous materials based on calcium phosphate, as is usual in this technical field. Specific materials are discussed more below, but the term "calcium phosphate" here includes the materials in the following non-limitative list:

α- and β-tricalcium phosphate
apatite
calcium dihydrogen phosphate and its hydrate
calcium hydrogen phosphate, anhydrous and hydrate
hydroxyapatite, including calcium deficient hydroxyapatite
carbonate apatite
dicalcium phosphate, anhydrous and dehydrate
fluoroapatite
monocalcium phosphate, anhydrous and monohydrate
octacalcium phosphate.

Two or more calcium phosphates may be employed in the granules of the material of the invention, either in different granules or mixed in each granule.

Particularly preferred calcium phosphate materials, which are resorbable, include, and are not limited to, stoichiometric hydroxyapatite with a Ca/P molar ratio of 1.667, a calcium deficient apatite with a Ca/P molar ratio of between 1.50 and 1.667, a chemically modified hydroxyapatite whereby one or more ions are substituted partially or completely by another ion or ions, and a chemically modified calcium-deficient apatite, whereby one or more ions are substituted partially or completely by another ion or ions. One example of these is a carbonate-substituted hydroxyapatite whereby carbonate ions substitute for phosphate and/or hydroxyl ions. A further example is a silicate-substituted hydroxyapatite whereby silicate ions substitute for phosphate ions. In some cases these ionic substitutions result in concomitant changes in the composition of the hydroxyapatite, such as loss of hydroxyl or calcium ions to retain charge balance. Another example is a silicate-substituted calcium deficient apatite whereby silicate ions substitute for phosphate ions, and the Ca/(P+Si) molar ratio is less than 1.667. Many other ionic substitutions can be made in the hydroxyapatite or calcium deficient hydroxyapatite material in the material of the current invention. These include, but are not limited to strontium, sodium, potassium, magnesium, barium, lithium, zinc, silver, titanium, cobalt, copper, nickel, iron, nitrate, sulphate, fluoride and chloride. The ions described above may substitute alone or in combinations. Some ions may substitute in a variety of valence states, and this may include substitution of e.g. silicate ions as $SiO_4^{4-}$, $Si_2O_7^{6-}$, $SiO_3^{2-}$ etc. either alone or in combination.

Other preferred calcium phosphates used in the invention include, but are not limited to, tricalcium phosphate (TCP), which can exist in either the beta- or the alpha-polymorph, or biphasic calcium phosphates (BCP), which consist of mixtures of hydroxyapatite and tricalcium phosphate phases. In the case of tricalcium phosphate, the production process described here that result in a material with values of the four parameters (CS, PS, TP and SA) as described above favours the formation of the beta-polymorph of TCP. However, the alpha polymorph may, in some cases, be obtained at lower temperatures than the normal high temperatures by addition of other ions (as described in the phase diagram of Nurse, J. Chem. Soc. 1959). The tricalcium phosphate phase may be modified whereby one or more ion is substituted partially or completely by another ion or ions, as described above for the cases of ion substituted hydroxyapatite and ion-substituted calcium-deficient hydroxyapatite. In the case of BCP, the relative proportion of the hydroxyapatite (HA) and tricalcium phosphate phases can vary from essentially 0% HA to 100% HA. The HA and/or the tricalcium phosphate phases in the BCP may be modified whereby one or more ion is substituted partially or completely by another ion or ions, as described above for the cases of ion-substituted hydroxyapatite and ion-substituted calcium-deficient hydroxyapatite.

Other calcium phosphates can be used in the current invention. For example, octacalcium phosphate, amorphous calcium phosphate, brushite, monetite and tetracalcium phosphate may be used alone or as additional phases in the above. Where the calcium phosphate is non-crystalline, the reference to crystal size herein is a reference to size of nano-particles of the material.

Other phases may be added to the calcium phosphates described above in the granules. Such other phases include but are not limited to, calcium carbonate, calcium sulphate, calcium silicate, calcium silicate glass, calcium silicate-based glass, calcium phosphate glass, calcium phosphate-based glass, calcium silicate-based glass-ceramic, calcium phosphate-based glass-ceramic, bioactive glasses, bioactive glass-ceramics, biocompatible glasses, biocompatible glass-ceramics, alumina and zirconia. Calcium phosphate-based materials in this list are not active in bone growth and are preferably absent. The amount of such other phases is preferably less than 50% by weight, more preferably less than 3% by weight. However it is preferred in the invention that the granules consist entirely or substantially entirely of calcium phosphate (e.g. ≥99% by weight).

In the method of producing the material of the invention, the calcium phosphate should preferably be dispersed in a liquid phase. This dispersion can result from the synthesis of the calcium phosphate material, such as by aqueous precipitation, or the calcium phosphate powder can be dispersed in a suitable solvent, typically water or a water based solvent. The calcium phosphate in the dispersion should have a small primary crystal size less than 100 nm, or optionally less than 80 or 90 nm, to form the material with values of the four parameters (CS, PS, TP and SA) as described above. The calcium phosphate may be present in the dispersion as primary crystals and/or as agglomerates of primary crystals.

One or more other phases may be included in the dispersion, if it is desired to incorporate an additional non-calcium phosphate material in the granules.

The calcium phosphate dispersed in a liquid phase is processed to form the material with values of the four parameters (CS, PS, TP and SA) as described above. The calcium phosphate dispersed in a liquid phase can be described as a suspension. The amount (grams, g) of solid phase (calcium phosphate) dispersed in the liquid phase (litres, L) can vary from 1500 g/L to 0.1 g/L, preferably between 150 g/L and 10 g/L.

The first processing step typically involves the dispersion being processed to remove the majority of the liquid phase to leave a wet compacted mass of the solid phase. The methods suitable for this step are vacuum filtration, using for example a Buchner funnel, filter paper and a vacuum pump (with or without a mass/force applied to the filtering compacted mass of the solid phase), a filter press, which applies a compaction pressure to the suspension effectively squeezing water out of the compacting mass of the solid phase, or centrifugation. In this step the removal of the liquid phase and the compaction of the mass of the solid phase is controlled to retain the appropriate total porosity (TP) after the subsequent drying step. If the compacted mass is allowed to compact too much, the total porosity may fall to levels below 60% or below 50%, and for the preferred range of total porosity of 70 to 90%, the process of removing the liquid phase must be controlled. This means not applying too high a vacuum force during vacuum filtration (or control of the mass/force applied during vacuum filtration), controlling the compaction force applied during filter pressing, or controlling the centrifugal force and duration during centrifugation. While these parameters can vary significantly depending on the equipment used, the amount of calcium phosphate in the dispersion, the type of liquid phase used, and the type of calcium phosphate used, the measure that a suitable set of processing conditions have been used in this first step is that the total porosity of the compacted mass of the solid phase, after drying at for example, but not limited to, between 50 and 150° C., measured using the ASTM C373, is greater than 50%, preferably greater than 60%, more preferably in the range of 70 to 90% of the total porosity. Typically, the drying step at between, but not limited to, 50 and 150° C., is to remove further water from the wet compacted mass of the solid phase to produce a dry compacted mass of the solid phase for further processing. Within the suspension, the interaction of the crystals of dispersed calcium phosphate in the liquid phase can be altered which will change the packing of the crystals within the compacted mass of the solid phase. Such alterations can be made by changing the pH of the liquid phase, or the addition of a surfactant, which may change the surface charge of the crystals and therefore the electrostatic charge between the crystals. This is another method of changing and/or controlling the total porosity (TP) and surface area (SA) of the bone graft system described herein.

The next processing step involves heating the dry compacted mass of the solid phase at a suitable temperature to remove any volatile components, and to control the crystal size (CS) and the pore size (PS) within the dry compacted mass of the solid phase to values with the ranges described above. This second step can be performed directly on the dry compacted mass of the solid phase obtained after the first processing step, or the dry compacted mass of the solid phase can be broken in to smaller pieces, or can be sized into the desired granule size (GS) range as described above. The temperature used to heat the sample is controlled so that the processes of crystal growth and sintering are either avoided or are only just commencing. This ensures that the crystal size (CS), pore size (PS) and surface area (SA) of the dry compacted mass of the solid phase retains values with the ranges described above. Typically, the temperature used for this heat treatment is between 200 and 1000° C., preferably, between 700 and 900° C. The duration of heat treatment at this temperature is typically 1-4 hours, but shorter or longer times are appropriate, provided the processes of crystal growth and sintering are either avoided or are only just commencing. The atmosphere for heating can be air, or may be an appropriate gas-enriched atmosphere, including water vapour. By utilising a heat treatment between 200 and 1000° C., preferably between 700 and 900° C., it can be achieved that the crystals in the compacted mass of the solid phase do not undergo sintering, so the final product is not classed as a ceramic. A ceramic is associated with an inorganic material that has undergone densification during high temperature heat treatment, and is associated with an increase in density and crystal size, and a decrease in total porosity and pore size. A ceramic is also associated with the formation of 'necks' between adjacent grains or crystals, with these adjacent grains or crystals appearing to be fusing together; this can be observed using SEM analysis. This is a different approach to other prior art, such as U.S. Pat. No. 6,511,510 and U.S. Pat. No. 7,942,934, which form ceramics by using elevated temperatures, namely 1000-1275° C. (preferably 1150-1250° C.) and 1050-1150° C., respectively.

The granular calcium phosphate material of the invention described herein can be sterilised using standard industry methods such as or ethylene oxide. The ionizing sterilisation methods gamma-irradiation, electron beam and X-ray sterilisation are also available.

The granular calcium phosphate material of the invention described herein can be used to treat a range of bone defects, bone trauma and bone fusions. For example, granules of the bone graft system can be packed into bone defects or placed into sites that require new bone to form, such as in posterolateral spinal fusion or in interbody spinal fusion. These granules can be implanted directly, or mixed with water, saline, blood or bone marrow aspirate, or another appropriate medium, prior to implantation. The granules may also be delivered as a paste or putty by mixing with an appropriate soluble carrier, such as but not restricted to resorbable polymers such as carboxymethyl cellulose or an ethylene oxide/propylene oxide block copolymer, or a natural polymer such as collagen or fibrin.

In addition, the granular calcium phosphate material of the invention described herein may be combined with active biomolecules such as growth factor proteins (such as bone morphogenetic proteins), antibiotics (such as gentamicin) or other pharmaceutical drugs, cytokines or antibodies.

In addition, the granular calcium phosphate material of the invention described herein may be combined with cells. This may be done in the operating theatre, immediately prior to implantation, or previously where the cells may be cultured for a period of time on the granules prior to implantation. Such cells include, but are not restricted to, autogenous mesenchymal stem cells, allogenic mesenchymal stem cells, osteoblast progenitor cells, osteoblast cells, endothelial cells, and combinations of these.

INTRODUCTION OF THE DRAWINGS

EMBODIMENTS OF THE INVENTION AND EXPERIMENTAL DATA

Figure 1:
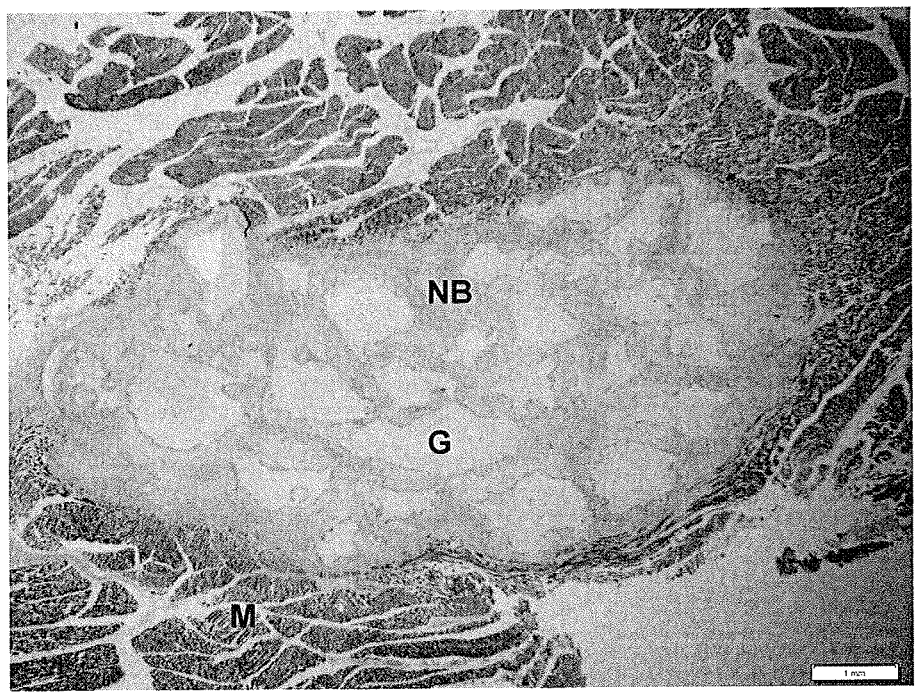
FIG. 1 is a light microscopy image of a histological section of the bone graft system of Example 2 of the invention, after implantation in muscle of a sheep, as described below.

The present invention is now illustrated with reference to the following non-limiting examples and accompanying figures.

Examples 1 to 4 describe production of examples of the granular materials of the invention. The average pore size of each of these materials is in the range 30-70 nm, measured by mercury porosimetry. The pores are in the size range 10-500 nm, with at least 50% of pores in the size range 10-100 nm, as seen in an SEM cross-section of the granule.

EXAMPLE 1

Production of the Bone Graft System 1 (Hydroxyapatite, HA)

A hydroxyapatite (HA) suspension consisting of approximately 50 g HA crystals dispersed in 500 ml alkaline aqueous solution (water with 10 ml ammonia solution added) is prepared by a conventional aqueous precipitation reaction. For the purpose of this example, this involves the drop wise addition of phosphoric acid solution to a calcium hydroxide suspension, with a Ca/P molar ratio of 1.667, and maintained at a pH of between 10 and 11, but other synthesis methods are appropriate. A wet compacted mass of the solid phase (hydroxyapatite) is obtained by removing the aqueous solution by passing the hydroxyapatite suspension through filter paper in a Buchner filter funnel attached on an Erlenmeyer flask with a side arm attached to a vacuum pump and collecting the solid phase. The critical control in this step is to control the removal of the liquid phase and the compaction of the mass of the solid phase to retain a high level of total porosity (TP). A vacuum pump was used to create a vacuum in the flask and the vacuum was created for a time such that about 80-90% by mass of the water was removed, thereby not over compacting the solid phase during the removal of the aqueous phase. In the current example the vacuum was created for only 30 minutes. The wet compacted solid phase was subsequently dried in an oven at 80° C.

The dried compacted mass of the solid phase (hydroxyapatite) was broken into smaller sizes using a mortar and pestle and a size range of granules between 1 and 2 mm were selected using a series of sieves. The total porosity of the granules in several samples prepared in this manner was measured using the method described in ASTM C373 and values were in a range of 74-84%. The granules were heated in a furnace at 700° C. for 1 hour. The total porosity of the heated granules was in the range of 66-76%, with a mean value of 71%.

The surface area (SA) of the granules, as measured by the BET method, was 27 $m^2/g$. Viewing the surface of the granules by SEM revealed that the dimensions of the crystals (CS) were in the range of 50-90 nm in the longest dimension, but with a shorter dimension of the crystal (width) ranging between 20 and 40 nm.

EXAMPLE 2

Production of the Bone Graft System 2
(Silicon-Substituted Hydroxyapatite, Si—HA)

A silicon-substituted hydroxyapatite suspension consisting of approximately 50 g Si—HA crystals dispersed in 500 ml alkaline aqueous solution (water with 10 ml ammonia solution added) is prepared by a conventional aqueous precipitation reaction. For the purpose of this example, this involves the drop wise addition of phosphoric acid solution to a calcium hydroxide suspension containing tetraethyl orthosilicate (TEOS), with a Ca/P molar ratio of 2.45 and a Ca/(P+Si) molar ratio of 1.64, and maintained at a pH of between 10 and 11, but other synthesis methods are appropriate. As for EXAMPLE 1, a wet compacted mass of the solid phase (silicon-substituted hydroxyapatite) is obtained by removing the aqueous solution by passing the silicon-substituted hydroxyapatite suspension through filter paper in a Buchner filter funnel attached on an Erlenmeyer flask with a side arm attached to a vacuum pump and collecting the solid phase. A vacuum pump was used to create a vacuum in the flask and the vacuum was created for a time such that about 80-90% by mass of the water was removed, thereby not over compacting the solid phase during the removal of the aqueous phase. In the current example the vacuum was created for only 30 minutes. The wet compacted solid phase was subsequently dried in an oven at 80° C.

The dried compacted mass of the solid phase (silicon-substituted hydroxyapatite) was broken into smaller sizes using a mortar and pestle and a size range of granules between 1 and 2 mm were selected using a series of sieves. The total porosity of the granules was measured using the method described in ASTM C373 and values were in a range of 73-82%. The granules were heated in a furnace at 900° C. for 1 hour. The total porosity of the heated granules was in the range of 71-78% with an average value of 75% (n=5).

The surface area (SA) of the granules, as measured by the BET method, was 28 $m^2/g$. Viewing the surface of the granules by SEM revealed that the longest dimensions of the crystals (CS) were in the range of 50-80 nm in the longest dimension, but with a shorter dimension of the crystal (width) ranging between 20 and 40 nm.

EXAMPLE 3

Production of the Bone Graft System 3
(Beta-Tricalcium Phosphate, β-TCP)

Using the methods described in EXAMPLES 1 and 2, a calcium-deficient apatite suspension consisting of approximately 50 g apatite crystals with a Ca/P molar ratio of 1.50 dispersed in 500 ml alkaline aqueous solution (water with 10 ml ammonia solution added) is prepared by a conventional aqueous precipitation reaction. For the purpose of this example, this involves the drop wise addition of phosphoric acid solution to a calcium hydroxide suspension, with a Ca/P molar ratio of 1.50, and maintained at a pH of between 7 and 8, but other synthesis methods are appropriate. The wet compacted mass of the solid phase (calcium-deficient apatite) is obtained and converted to a dry compacted mass and then to granules by the same process as described in EXAMPLES 1 and 2. The granules, with a total porosity greater than 65% are heated at 750° C. for 1 hour. X-ray diffraction analysis revealed the phase composition to be of the beta-polymorph of tricalcium phosphate. The total porosity of the heated granules was in the range of 65-77% (n=5).

The surface area (SA) of the granules, as measured by the BET method, was 25 $m^2/g$. Viewing the surface of the granules by SEM revealed that the longest dimensions of the crystals (CS) were in the range of 50-90 nm in the longest dimension, but with a shorter dimension of the crystal (width) ranging between 20 and 50 nm.

EXAMPLE 4

Production of the Bone Graft System 4 (Biphasic Calcium Phosphate, BCP)

Using the methods described in EXAMPLES 1, 2 and 3, a calcium-deficient apatite suspension consisting of approximately 50 g apatite crystals with a Ca/P molar ratio of 1.58 dispersed in 500 ml alkaline aqueous solution (water with 10 ml ammonia solution added) is prepared by a conventional aqueous precipitation reaction. For the purpose of this example, this involves the drop wise addition of phosphoric acid solution to a calcium hydroxide suspension, with a Ca/P molar ratio of 1.58, and maintained at a pH of between 8 and 10, but other synthesis methods are appropriate. The wet compacted mass of the solid phase (calcium-deficient apatite) is obtained and converted to a dry compacted mass and then to granules by the same process as described in EXAMPLES 1 and 2. The granules, with a total porosity greater than 65% is heated at 800° C. for 1 hour. X-ray diffraction analysis revealed the phase composition to be a biphasic mixture of the beta-polymorph of tricalcium phosphate and hydroxyapatite (in approximately a 50:50% ratio). The total porosity of the heated granules was in the range of 68-79%, with an average value of 73% (n=5).

The surface area (SA) of the granules, as measured by the BET method, was 22 $m^2/g$. Viewing the surface of the granules by SEM revealed that the longest dimensions of the crystals (CS) were in the range of 50-80 nm in the longest dimension, but with a shorter dimension of the crystal (width) ranging between 20 and 40 nm.

EXAMPLE 5

Protein Adhesion to the Bone Graft Systems of 1-4

To test the effect of the crystals and pore sizes, and the high values of surface areas, of the bone graft systems of EXAMPLES 1-4, a measurement of the amount of serum proteins from a 3 ml solution of 1% foetal bovine serum that adheres to 0.5 g of the granules after 24 hours of soaking was made. As a comparison, a porous hydroxyapatite granule with a similar total porosity to the granules of EXAMPLES 1-4, but a crystal size of approximately, 1 µm, a pore size greater than 1 µm and a surface area of 1.5 $m^2/g$ was tested (termed CONTROL granules). Using the bicinchoninic acid (BCA) assay to measure the amount of proteins present in the initial 1% foetal bovine serum solution and in the solutions after soaking the granules, the amount of serum proteins adhered to the granules can be calculated as the difference of these two values. The amount of serum proteins adhered to granules produced by EXAMPLES 1-4 was 39%±5% of the total proteins in the original 1% foetal bovine serum solution, whereas the CONTROL granules adsorbed 9%±3% of the proteins.

EXAMPLE 6

Demonstration of Osteoinductivity of the Bone Graft System

The bone graft system described in EXAMPLE 2 was implanted into small defects in the muscles in the backs of 18 month old sheep. After 6 weeks, the explanted specimens/sections were processed for histology and stained (tetrachrome) to identify new bone formation. Images showed new bone (stained blue) had formed around the granules and throughout the defect (FIG. 1). A comparative non-osteoinductive synthetic bone graft (available as ProOsteon 200R) showed no new bone after this implantation time, and only the presence of dense fibrous tissue surrounding the granules.

FIG. 1 shows tetrachrome stained histology of the bone graft system described in EXAMPLE 2 implanted intramuscularly in sheep for 6 weeks showing decalcified granules (G) of the bone graft system, host muscle (M) and new bone (NB) formed around the granules within the implant site.

Figure 2:
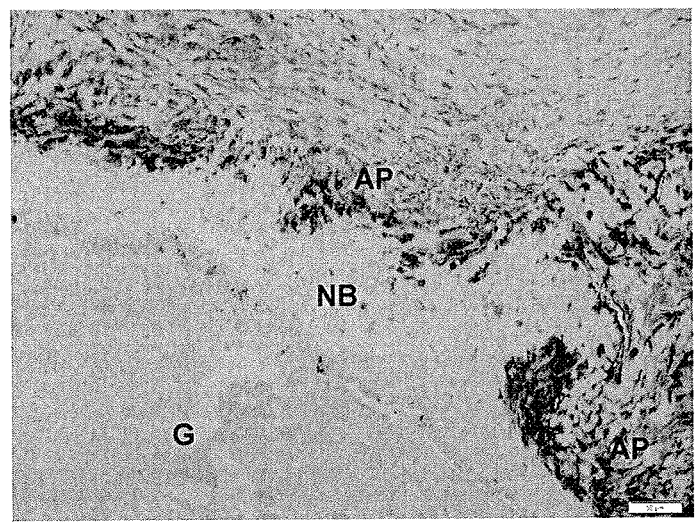
FIG. 2 is a light microscope image showing alkaline phosphatase expression by cells at an area of new bone formation at the surface of implanted granules of the bone graft system of Example 2.

Decalcified histology slides were stained using immunohistochemistry to show positive expression of alkaline phosphatase (AP), a specific marker of osteoblast cells differentiation and therefore bone formation; cells positively stained for AP appear brown. Such a stained section is shown in FIG. 2, where cells (osteoblasts) positively stained for AP appear at the location of new bone formation (NB) at the surface of the granules (G) in the experiment in Example 6. This indicates that new bone has formed by the recruitment of host mesenchymal stem cells to the intra-muscular implantation site and their differentiation to osteoblast cells, where they produce new bone. There is no evidence of the presence of significant regions of chondrocytes/cartilaginous tissue in these sections, so that the new bone appears to form from a direct route, rather than via a cartilage intermediate phase as is observed in endochondral bone formation.

Figure 3:
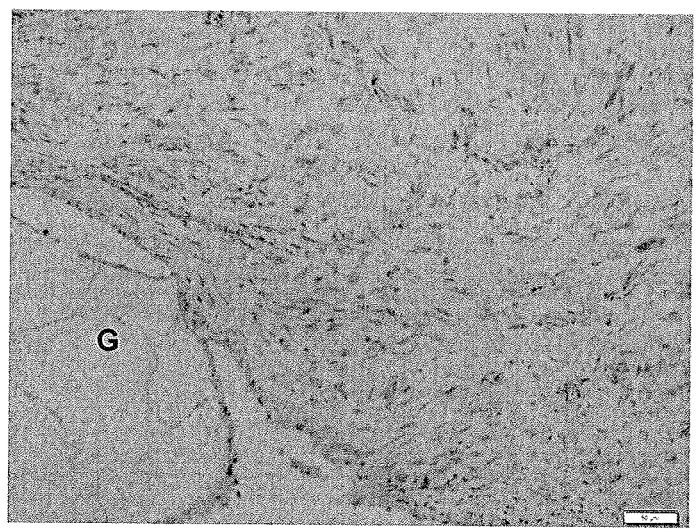
FIG. 3 is a light microscope image showing no alkaline phosphatase expression in the vicinity of implanted granules of a prior art system, used for control.

In contrast, a non-osteoinductive synthetic bone graft (ProOsteon 200R) showed no osteoblast cells positively stained for AP after this implantation time, and only the presence of dense fibrous tissue (fibroblasts) surround the granules (FIG. 3).

FIG. 2 is a microscope image (×20) showing alkaline phosphatase (AP) expression by cells (stained brown) at the area of new bone formation (NB) at the surface of granules (G) of the nanoscale bone graft system described in EXAMPLE 2, implanted intramuscularly in sheep for 6 weeks.

FIG. 3 is a microscope image (×20) showing no alkaline phosphatase (AP) expression by cells (lack of brown staining) in the vicinity of granules (G) of ProOsteon 200R used as an osteoconductive control, implanted intramuscularly in sheep for 6 weeks.

Figure 4:
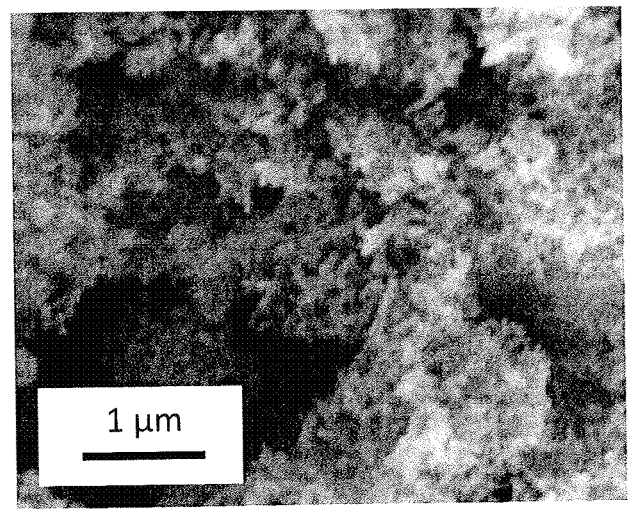
FIG. 4 is a scanning electron microscope image (SEM) showing the surface of granules in the bone graft system of Example 2.

FIG. 4 shows a scanning electron microscope (SEM) image of the surface of granules of the nanoscale bone graft system described in EXAMPLE 2, showing the nanoscale structure, including size and shape, of the crystals making up the granules.

Figure 5:
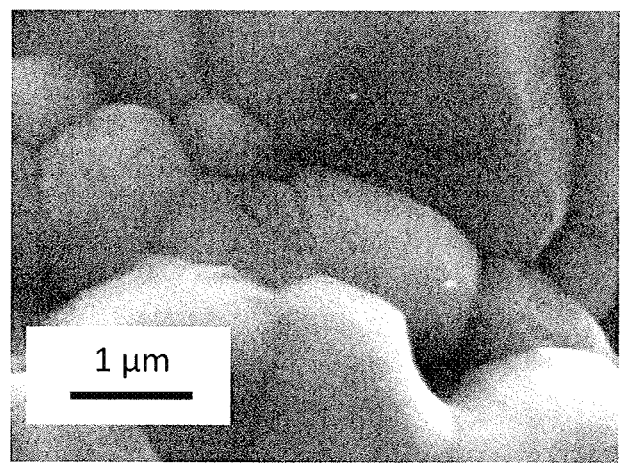
FIG. 5 is a SEM image of the surface of granules of a comparative hydroxyapatite sintered ceramic material.

FIG. 5 shows a scanning electron microscope (SEM) image of the surface of granules of a comparative macroporous hydroxyapatite ceramic material, showing the lack of nanoscale pore structure and the presence of fused large grains that have sintered together making up the granules.

The invention claimed is:

1. A porous granular calcium phosphate material, comprising discrete porous granules each containing crystals of at least one calcium phosphate, wherein
   (i) at least 90% of said crystals of the granules have a crystal size in the range 1.0-100 nm, where the crystal size is the longest dimension of the crystal as seen in a cross-sectional SEM,
   (ii) at least 90% of the pores in the granules have a pore size in the range 10-500 nm, wherein the pore size is the longest dimension of the pore as seen in a cross-sectional SEM,
   (iii) the average pore size of the pores having pore size in the range 10-500 nm in the granules is in the range 30-90 nm, as measured by mercury intrusion porosimetry,
   (iv) the total volume porosity of the granules, measured using Archimedes's principle, is at least 50%, and
   (v) the surface area of the granules, measured by the BET method, is in the range 1 0-70 $m^2/g$,
   wherein at least 90% of said crystals have at least one dimension of not more than 50 nm as seen in a cross-sectional SEM, and
   wherein said crystals of said granules are in a substantially unsintered stat.

2. A calcium phosphate material according to claim 1 wherein at least 90% of said crystals has at least one dimension in the range 20-40 nm as seen in a cross-sectional SEM.

3. A calcium phosphate material according to claim 1 wherein the average ratio of said longest dimension of each crystal to the shortest dimension thereof is in the range 1-10.

4. A calcium phosphate material according to claim 1 wherein at least 50% of the pores in the granules have said pore size in the range 10-100 nm.

5. A calcium phosphate material according to claim 1 wherein said average pore size of the pores having pore sizes in the range 10-500 nm in the granules is in the range 30-70 nm.

6. A calcium phosphate material according to claim 1 wherein the total volume porosity of the granules is in the range 70-90%.

7. A calcium phosphate material according to claim 1 wherein the surface area of the granules is in the range 20-40 $m^2/g$.

8. A calcium phosphate material according to claim 1 wherein the or each calcium phosphate of said granules is selected from:
- stoichiometric hydroxyapatite,
- calcium-deficient hydroxyapatite,
- stoichiometric or calcium-deficient hydroxyapatite, wherein one or more ions is substituted partially or completely,
- tricalcium phosphate, and
- biphasic calcium phosphate consisting of hydroxyapatite and tricalcium phosphate phases.

9. A calcium phosphate material according to claim 1 having osteoinductivity when implanted in a non-osseous site in a mammal.

10. A method of treatment of a mammal by bone growth, comprising placing a calcium phosphate material according to claim 1 at a site at which the bone growth is to take place.

11. A method of making a calcium phosphate material according to claim 1, comprising the steps of:
(a) preparing a dispersion of calcium phosphate crystals in a liquid phase,
(b) partially removing the liquid phase to obtain a wet compacted mass comprising the calcium phosphate crystals,
(c) drying said wet compacted mass obtained in step (b) so as to remove the liquid phase and obtain dried material in the form of a dry compacted mass comprising the calcium phosphate crystals wherein the dry compacted mass has a total porosity of not less than 60%, as measured by Archimedes's method, prior to the heat treating step (d),
(d) heat treating said dried material obtained in step (c), at a temperature in the range 200 to 1000° C. while substantially avoiding sintering of the crystals, and
(e) before or after step (d), dividing the dry compacted mass into granules.

12. A calcium phosphate material according to claim 3 wherein the average ratio of said longest dimension of each crystal to the shortest dimension thereof is in the range of 1.5-3.

13. A method according to claim 11, wherein in step (d) said heat treating of said dried material obtained in step (c) is at a temperature in the range 700 to 900° C., while substantially avoiding sintering of the crystals.

* * * * *